United States Patent [19]

Incorvaia

[11] 4,401,113
[45] Aug. 30, 1983

[54] SPONGE SPLINT COMPRESSION DRESSING

[76] Inventor: Anthony I. Incorvaia, 5659 Melvin St., Pittsburgh, Pa. 15217

[21] Appl. No.: 302,038

[22] Filed: Sep. 14, 1981

[51] Int. Cl.³ ............................................. A61L 15/00
[52] U.S. Cl. .................................... 128/156; 128/165
[58] Field of Search ............. 128/155, 156, 157, 87 R, 128/89 R, 83, 82, 165, 166

[56] References Cited

U.S. PATENT DOCUMENTS

| | | | |
|---|---|---|---|
| 2,858,731 | 11/1958 | Robins | 128/156 |
| 3,780,731 | 12/1973 | Quello | 128/156 X |
| 3,989,041 | 11/1976 | Davies | 128/166 |
| 4,133,311 | 1/1979 | Karczewski | 128/166 |

Primary Examiner—John D. Yasko
Attorney, Agent, or Firm—Webb, Burden, Robinson & Webb

[57] ABSTRACT

A combination splint-compression dressing for an injured joint comprises a regenerated, cellulosic sponge formed to a predetermined shape to totally encapsulate the injured joint. The cellulosic sponge is hydrophilic and sufficiently open celled and porous so as to be highly absorbent through capillary action. An outer layer of a nonwoven resin impregnated web of organic fibers is bonded to the cellulosic sponge so as to provide temperature insulation and impart dimensional stability to the sponge. The sponge totally envelops the injured area and is used both for first aid and rehabilitation.

4 Claims, 3 Drawing Figures

SPONGE SPLINT COMPRESSION DRESSING

BACKGROUND OF THE INVENTION

My invention relates to the treating of injuries and, more specifically, to a combination splint and compression dressing for treating sprained or otherwise injured or inflamed body joints or members such as the ankle, knee, shoulder, elbow and wrist.

DESCRIPTION OF THE PRIOR ART

A common injury treated in the field of sports medicine and emergency rooms alike is the trauma to muscles, connective tissue and bone results in sprained joints, pulled muscles and bruised tissue. These injuries are considered acute injuries in that they have a short onset and a short duration when properly managed with immediate and follow-up procedures.

Immediate injury management of these conditions consist of cold application, compression, elevation and immobilization. The first three procedures are standard first aid procedures and when used together are designed to decrease hemorrhage and the effusion of fluids at the injury site. The application of cold also decreases inflammation, muscle spasm and pain. Thereafter, heat is used for post acute conditions of sprains, strains and contusions. Heat increases circulation, encourages venous and lymphatic drainage and as a result hastens cell metabolism and healing. It also reduces spasm in muscles by temporarily inhibiting the nerve activity to those muscles.

The cold application, compression and immobilization are presently conducted with the benefit of a number of different medical procedures and apparatus. The application of cold is carried out through the use of ice bags and the like. Compression can be achieved through various forms of air splints which vary from simple balloon-like devices blown up in seconds to complex extremity pumps used to provide rhythmic, intermittent pressure to remove edematous fluid by driving it back into the venous system. These various types of commercial air splints have a number of drawbacks, including that they have to be blown up and that they readily leak or develop holes. The injured limb has to be placed in the splint which often causes additional discomfort. The air splints are normally constructed of plastic which is not moisture vapor permeable and, therefore, causes the skin, which is in contact therewith to stick to the splint. Thus, the splints can be used only for immobilization procedures.

Individual pieces of sponge dipped in ice water and applied firmly over the swollen joint area have also been tried. Where the sponge was tightly secured to the injured area, the swelling was often forced from the area immediately subjacent the sponge and into adjacent areas thereby increasing the swelling problem rather than decreasing it.

Exemplary of a rigid joint immobilizing temporary splint is U.S. Pat. No. 3,800,789. Exemplary of a splint made in layers is U.S. Pat. No. 3,695,258. Exemplary of patents which relate to blocks of foam to allow for insertion of a body limb are U.S. Pat. Nos. 3,901,228 and 3,903,878. The absorptive qualities of regenerated cellulose are known for medicinal use, see U.S. Pat. No. 4,198,968. Finally, the presently preferred composition is known and is used for scouring pads in the kitchen.

SUMMARY OF THE INVENTION

I have now provided a single dressing which accommodates cold or hot application, provides for compression and likewise provides for immobilization of the injured area. The dressing is reusable, is portable, is inexpensive and can be sterilized by boiling. Minimal expertise is required to use and apply the dressing. The dressing can be applied immediately to the injury thereby controlling swelling so the physician can determine the extent of the actual damage without having to wait several days for the swelling to go down. The dressing is very beneficial where the injured must travel and the application of the dressing causes no undue pain as in a stationary type splint. The dressing finds particular application in the field of sports medicine but is equally applicable to emergency room treatment of nonsport related injuries. The dressing can be used both for first aid procedures and rehabilitation.

My invention is a combination splint-compression dressing for an injured joint or the like of the body comprising a sponge formed to a predefined shape to totally envelop the injury. The sponge is fibrous, hydrophilic, coarse and porous so as to be highly absorbent through capillary action. Regenerated cellulose sponge has been found to be the best sponge having these necessary characteristics. Preferably an outer layer of a nonwoven resin impregnated web of organic fiber is bonded to the sponge so as to provide durability, heat insulation, rigidity and dimensional stability thereto. In the preferred embodiment, the sponge layer is from one-half to one inch and the web layer is one-quarter of an inch thick. The method of treating an injury with said dressing also forms a part of this invention.

DESCRIPTION OF THE PREFERRED EMBODIMENTS

The major constituent in my combination splint and compression dressing is the sponge material. This material must be hydrophilic. It must be capable of substantial swelling when wet. It must be generally chemically inert to water and topically applied medicines used for the rehabilitation of joint injuries. It must be coarse, porous and fibrous and quite absorbent so that liquid or fluid can be carried through the entire network by capillary action. It must be capable of being saturated with liquid. It must retain water even under a dead load condition and it must have the capability to uniformly disperse liquid so as to get good heat transfer from the sponge to the injured area being treated.

The material, which meets all of the above requirements, is a regenerated cellulose sponge. This material has a bulk density on the order of 0.6–0.7 gr./cc and an absorption capacity on the order of 1.7 ml./cc. The preferred thickness is one-half to two inches and the most preferred thickness is one-half to one inch.

In order to give dimensional stability to the sponge, an outer layer of an open celled, low density, nonwoven organic fiber is provided. These fibers such as nylon are unified preferably by an organic binder which binds the web fibers firmly together at points where they intersect and contact one another. it is generally desirable for the web to have a bulk density between 0.05 and 0.2 gr./cc and the web fibers to have a thickness between 5 and 50 denier. The web is superimposed on the sponge and fusion bonded thereto so at least part of the fibers of the web along the interface are embedded in the sponge material to form a strong bond. In addition to lending dimensional stability to the cellulose sponge, the outer layer or nonwoven fibrous web lends durability, strength, rigidity and an insulating quality to the overall dressing.

Figure 1:
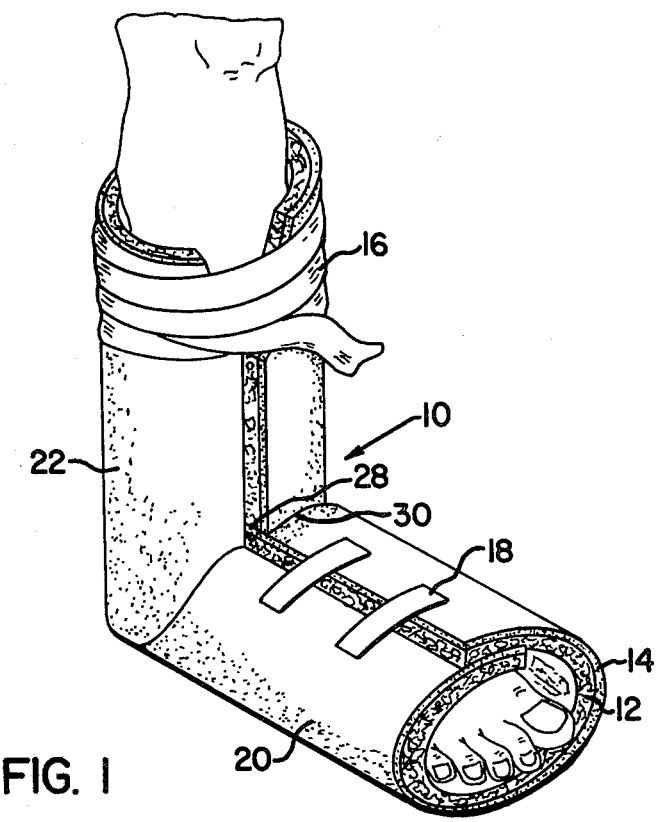
FIG. 1 is a perspective view illustrating the dressing as applied to an ankle injury.
Figure 2:
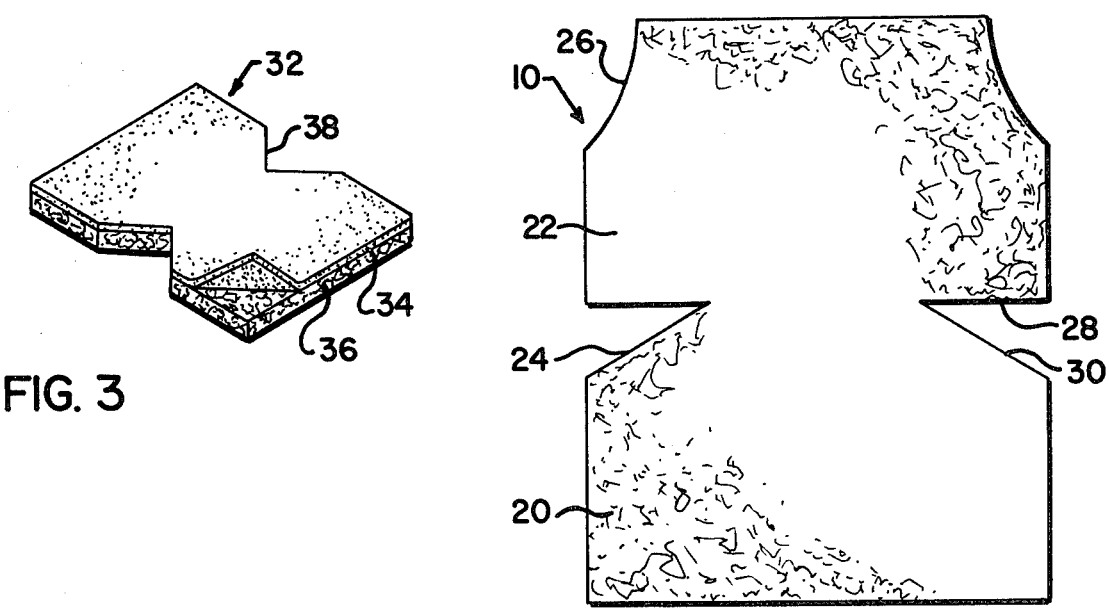
FIG. 2 is a plan view of the dressing of FIG. 1 prior to application to the injured area.

It is also important for the combination splint-compression dressing to have sufficient surface area to cover the entire injured area and the immediate area adjacent thereto. A sponge splint compression dressing is shown applied to a sprained ankle in FIG. 1. The dressing, generally designated 10, preferably comes in sheet form and for an ankle injury is preformed to the configuration shown in FIG. 2. Specifically, the inner layer of regenerated cellulose sponge 12 is fusion bonded to the outer nonwoven, fibrous web 14. The dressing includes a substantially rectangular foot section 20 connected to an ankle section 22 through a tapered connecting section 24. The upper end of the ankle section 22 includes arcuate side trims 26 along opposing sides.

The injured foot is placed against the sponge side of the dressing on the foot section 20 which is folded over the foot with the toes being uncovered for observation purposes. Thereafter, the ankle section 22 is folded around the upper portion of the ankle with the end of the ankle section 28 overlapping the top of the foot section 30 in the immediate area of the ankle where ligament damage occurs. Note that the dressing extends from the metatarsal-phalangeal joints of the toes and foot distally to the area proximal above the area of the ankle where swelling takes place. This way the entire area is exposed to the compression and all the edema in the area is flushed out. The dressing can be held in place by standard wrapping such as the elastic wrap illustrated at 16 in FIG. 1 or by means of Velcro strips 18 as illustrated for the foot area in FIG. 1. The use of the elastic wrap provides more rigidity and equalized compression whereas the Velcro strip provides for ease of application.

Figure 3:
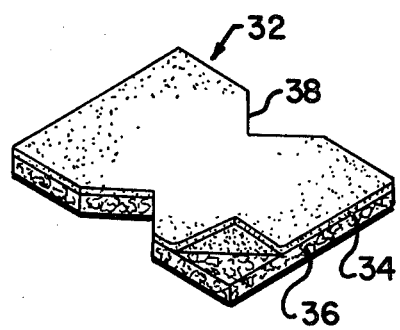
FIG. 3 is a perspective view of a dressing for use on an injured elbow.

Such a dressing is equally applicable to other joints and one such dressing, generally designated 32, is illustrated in FIG. 3 for an elbow. This dressing, which is substantially rectangular, is likewise made up of an inner layer of regenerated cellulose sponge 36 and an outer layer of nonwoven fibrous web 34 bonded thereto. The layers are shown as separated only to illustrate that two layers are present and in practice they are fusion bonded and difficult to separate. The dressing 32 includes angular cutouts 38 on two opposing sides so that as the elbow is placed in the sponge dressing 32, it is easily foldable so as to form about the elbow area. Such a dressing is then appropriately wrapped or held with Velcro strips or the like as for the embodiment illustrated in FIG. 1.

The combination dressing is applied as follows. Where the injury has just occurred, the dressing, which normally is first rinsed out, is moistened with cool water and properly wrapped around the injured area such as the ankle. A portion of the dressing is wrapped with elastic wrap so as to permanently secure it to the foot. Thereafter, the entire dressing is wrapped so as to cover up the rest of the ankle and skin. The elastic wrap covers up the dressing in its entirety but the toes are left open to watch for circulatory impairment. At this point the first aid treatment has been completed and the dressing will prevent swelling from occurring as well as act as a splint. Subsequent treatment obviously depends on the severity of the injury.

Where the injury has taken place some time ago and swelling is already present or an immediately treated injury is severe and persists, rehabilitation can also be accomplished with the dressing. The initial steps as just described for first aid treatment are also carried out as the initial rehabilitation steps. Thereafter the foot and ankle are submerged in cold water or ice water for about ten minutes. They are then removed and the excess water is squeezed from the sponge and wrap. The person's limb is elevated as much as possible or at least to the same level as the rest of the body. The foot and ankle are kept out of the water for about ten minutes or until the previously submerged area attains normal temperature conditions. The submersion and thawing procedures are repeated three or four times in succession. The compression caused by the water in the sponge flushes out the swelling and aids circulation. The flushing action can be aided by slight flexion and extension of the toes which creates a pumping effect. As the person starts to make progress between treatments, more intense exercise for the limb is performed.

During later treatments the limb and sponge dressing are used in warm water for short periods of time for compression purposes and also for the physiological effects of the heat. Normally the dressing is kept off at night to avoid skin maceration. A dry wrap can be applied where compression and constant immobilization is required.

It will be recognized that my dressing and method of treating an injury with the dressing finds primary application in the treating of body joints. However, it will also be recognized that injuries causing swelling to various parts of the arms and legs other than the joints can likewise be treated with my combination splint-compression dressing.

Modifications to the preferred embodiments described above may be made without departing from the spirit and scope of the invention as set forth in the following claims.

I claim:

1. A combination splint-compression dressing for an injured ankle or foot comprising a preformed two layer sheet, the inner layer being a regenerated, open celled, swellable, cellulose sponge of about one-half inch and the outer layer being a nonwoven resin impregnated web of organic fibers of about one-quarter inch thick bonded to said inner layer, said dressing being formed with a foot section to foldably cover the foot area, an ankle section joined to the foot section through a tapered connecting section and a foldable section to cover the ankle area and overlap the foot area, said dressing being bendable in the area of the connecting section so as to permit the ankle section to bend at substantially right angles to the foot section.

2. The combination of claim 1, said sponge being a regenerated cellulose, capable of retaining water even under dead load conditions and having a bulk density on the order of 0.6 gr./cc–0.7 gr./cc and an absorption capacity on the order of 1.7 ml./cc.

3. The combination of claim 1, said web having a bulk density of 0.05 to 0.2 gr./cc and a fiber thickness of 5 to 50 denier.

4. The combination of claim 1, said web comprising nylon fibers.

* * * * *